(12) United States Patent
Hein et al.

(10) Patent No.: US 9,788,590 B2
(45) Date of Patent: Oct. 17, 2017

(54) NOISE REDUCTION ELEMENTS

(71) Applicants: Steven A. Hein, Sedona, AZ (US); Darryl C. Bassani, Yorba Linda, CA (US)

(72) Inventors: Steven A. Hein, Sedona, AZ (US); Darryl C. Bassani, Yorba Linda, CA (US)

( * ) Notice: Subject to any disclaimer, the term of this patent is extended or adjusted under 35 U.S.C. 154(b) by 338 days.

(21) Appl. No.: 14/586,708

(22) Filed: Dec. 30, 2014

(65) Prior Publication Data

US 2015/0107936 A1 Apr. 23, 2015

Related U.S. Application Data

(62) Division of application No. 13/306,195, filed on Nov. 29, 2011, now Pat. No. 8,931,118.

(51) Int. Cl.
| | |
|---|---|
| *A61F 11/14* | (2006.01) |
| *A42B 3/16* | (2006.01) |
| *G10K 11/16* | (2006.01) |
| *G10K 11/178* | (2006.01) |

(52) U.S. Cl.
CPC .............. *A42B 3/163* (2013.01); *A42B 3/16* (2013.01); *A42B 3/166* (2013.01); *A61F 11/14* (2013.01); *G10K 11/16* (2013.01); *G10K 11/1788* (2013.01); *G10K 2210/128* (2013.01); *G10K 2210/509* (2013.01)

(58) Field of Classification Search
CPC .... A61F 11/14; A61F 2011/145; A61F 11/06; A61F 11/12; G10K 11/16; G10K 11/175; G10K 11/1788; G10K 2210/509; G10K 11/168; G10K 11/172; A42B 3/16; A42B 3/163; A42B 3/166; H04R 1/1058; H04R 1/1083

USPC ..... 2/209, 423; 181/129; 381/374, 379, 371, 381/372, 376
See application file for complete search history.

(56) References Cited

U.S. PATENT DOCUMENTS

| | | | | | |
|---|---|---|---|---|---|
| 2,345,842 | A | * | 4/1944 | Valentine | A61F 11/08 128/866 |
| 2,468,267 | A | * | 4/1949 | Mondl | H04R 1/1008 2/209 |
| 2,468,721 | A | * | 4/1949 | Volkmann | H04R 1/1008 181/129 |
| 3,021,526 | A | * | 2/1962 | Lastnik | A42B 3/166 181/129 |
| 3,091,771 | A | * | 6/1963 | Bixby | A42B 3/166 2/423 |
| 3,178,723 | A | * | 4/1965 | Aileo | A42B 3/166 2/209 |

(Continued)

OTHER PUBLICATIONS

Brown, Charles H., and Gordon, Michael S., Motorcycle Helmet Noise and Active Noise Reduction, The Open Acoustics Journal 2011, vol. 4, p. 14-24.

(Continued)

*Primary Examiner* — Amy Vanatta
(74) *Attorney, Agent, or Firm* — Knobbe Martens Olson & Bear LLP

(57) ABSTRACT

A motorsports helmet having an isolation mount defining a receptacle is provided. An adjustment plate is selectively disposed within the receptacle at different depths and includes an ear-cup. The ear-cup is secured relative to the adjustment plate and includes at least two degrees of freedom of movement.

20 Claims, 4 Drawing Sheets

(56) References Cited

U.S. PATENT DOCUMENTS

| | | | | |
|---|---|---|---|---|
| 3,456,263 A * | 7/1969 | Aileo | A42B 3/16 | 2/209 |
| 3,470,564 A * | 10/1969 | Aileo | A42B 3/166 | 2/209 |
| 3,535,710 A * | 10/1970 | Aileo | A61F 11/14 | 2/209 |
| 3,621,488 A * | 11/1971 | Gales | A42B 3/166 | 181/129 |
| 3,833,939 A * | 9/1974 | Dostourian | H04R 1/1066 | 2/209 |
| 3,845,505 A * | 11/1974 | Davison | A42B 3/166 | 2/209 |
| 3,918,098 A * | 11/1975 | Devaney | A42B 3/166 | 2/209 |
| 4,133,053 A * | 1/1979 | Lundin | H04R 1/1058 | 2/209 |
| 4,453,277 A * | 6/1984 | Durand | A42B 3/14 | 2/416 |
| 4,523,661 A * | 6/1985 | Scalzo | A42B 3/166 | 181/129 |
| 4,905,322 A * | 3/1990 | Aileo | A42B 3/166 | 181/129 |
| 5,003,631 A * | 4/1991 | Richardson | A42B 3/166 | 2/413 |
| 5,035,005 A * | 7/1991 | Hung | H04M 1/05 | 2/209 |
| 5,278,999 A * | 1/1994 | Brown | A61F 9/025 | 2/10 |
| 5,500,958 A * | 3/1996 | Falco | A61F 11/14 | 2/209 |
| 5,519,783 A * | 5/1996 | Kumar | H04R 1/1008 | 181/129 |
| 5,996,123 A * | 12/1999 | Leight | A61F 11/14 | 128/867 |
| 2005/0117754 A1 | 6/2005 | Sakawaki | | |
| 2007/0033029 A1 | 2/2007 | Sakawaki | | |
| 2010/0095439 A1 | 4/2010 | Nolan et al. | | |

OTHER PUBLICATIONS

Jelsoft Enterprises, Ltd., Noise cancellation headphones integrated into a helmet step-by-step install—ADVrider,http://advrider.com/forums/showthread.php?t=367454&highlight=Noise+cancellation+headphones+integrated, Copyright ADVrider 2011.

* cited by examiner

NOISE REDUCTION ELEMENTS

CROSS-REFERENCE TO RELATED APPLICATIONS

This is a divisional of U.S. application Ser. No. 13/306,195, filed on Nov. 29, 2011, entitled MOTORSPORTS HELMET WITH NOISE REDUCTION ELEMENTS, which is hereby incorporated by reference in its entirety.

BACKGROUND OF THE INVENTION

Field of the Invention

This invention relates generally to a variety of motorsports helmets. More particularly, the invention relates to a motorcycle helmet with noise reduction elements.

Description of the Related Art

A motorcyclist's ability to hear while riding is a critical safety factor in the modern environment. Unfortunately, a motorcyclist's hearing may be impeded by engine noise, wind noise and helmet design, among other things. High noise levels, such as those experienced by motorcyclists, may increase fatigue, may impair reaction times and may impede attention, effectively reducing the safety of the motorcyclists and those around him or her. Moreover, high intensity noise over long periods of time may have long-term consequences on a motorcyclist's hearing ability. At highway speeds, noise levels may easily exceed 100 dB even when wearing a traditional helmet. This is particularly troublesome for daily motorcyclists as well as occupational motorcyclists, such as police officers.

To combat the noise, some motorcycle helmets use sound deadening material around the area of the ears. Other motorcyclists may opt to use earplugs to reduce noise and prevent noise induced hearing loss. In both cases, the motorcyclist's hearing may be protected, but it is also impaired such that the motorcyclist may not be able to hear other cars, people, sirens, etc. around him or her.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional helmets.

One aspect of the present invention is a motorcycle helmet that has a shell, an isolation mount disposed in the shell and having a receptacle, and an adjustment plate disposed within the receptacle. The helmet further includes a coupling secured to the adjustment plate and an ear-cup secured to the coupling.

Another aspect of the invention is a passive noise cancellation system. The system has an isolation mount having a receptacle, an adjustment plate at least partially disposed in the receptacle, and an engagement structure disposed so as to inhibit movement of the adjustment plate through the receptacle.

Another aspect of the invention is a method of reducing noise in a motorcycle helmet. The method includes providing a shell having an isolation mount and an adjustment plate, the isolation mount defining a receptacle configured to receive at least a portion of the adjustment plate at a plurality of positions and engaging the adjustment plate with the isolation mount so as to select one of the plurality of positions.

DETAILED DESCRIPTION OF THE PREFERRED EMBODIMENTS

Figure 1:
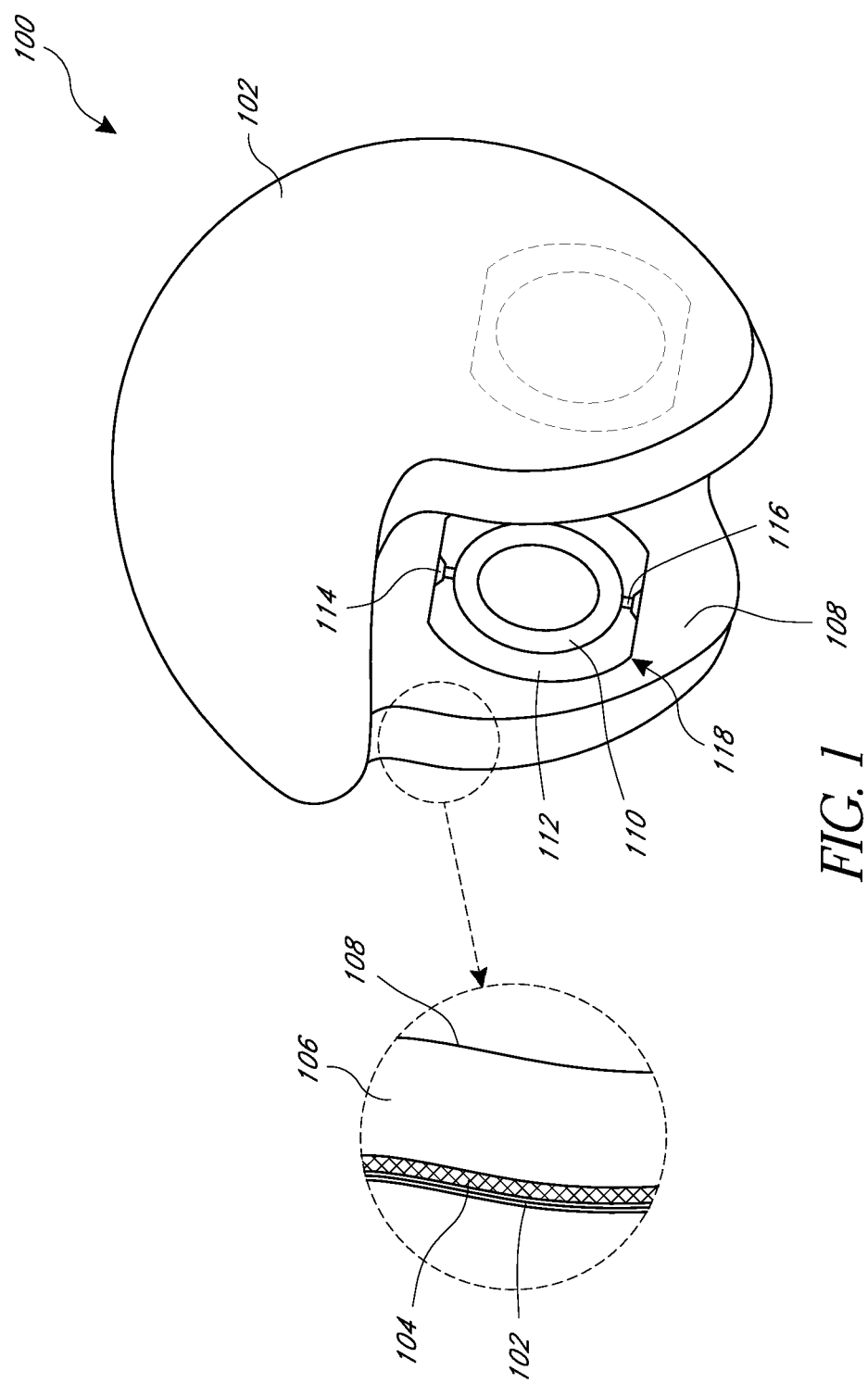
FIG. 1 is a perspective view of a motorcycle helmet with a passive noise reduction system.

The preferred embodiments of the present invention will now be described with reference to the accompanying figures, wherein like numerals refer to like elements throughout. The terminology used in the description presented herein is not intended to be interpreted in any limited or restrictive manner simply because it is being utilized in conjunction with a detailed description of certain specific preferred embodiments of the present invention.

Noise affecting a motorcyclist may have many sources, such as engine noise, road noise, other vehicle noise and wind noise. As the speed of a motorcycle increases, typically the most prominent source of noise is wind noise. Common to all types of noise experienced by a rider are vibrations that make their way to a rider's ear. In some cases, a helmet may increase the perceived amplitude of noise by transmitting vibrations from the environment directly to a rider's ear. For example, as a motorcyclist travels faster, the wind impacting the shell of his or her helmet will in turn create more vibration that the motorcyclist perceives as noise. This effect increases dramatically as speed increases. As discussed above, several methods for reducing noise in a motorcycle helmet exist, but they are mostly limited to sound suppression, which can be dangerous for a rider. These previous solutions fail to address the primary driver of helmet noise, which is the coupling of noise related vibrations to a rider's ear.

A typical helmet is comprised of several layers, including a shell, a shock-absorbing layer, and a comfort layer. A helmet's shell is the outermost layer and is typically made from resilient, water-resistant materials such as plastic and fiber composites. A helmet's shock-absorbing layer, which is its primary safety layer, may be made out of a rigid, but shock-absorbing material such as expandable polystyrene foam. Although not typical, a helmet's fire-proof layer may be integrated and made of a closed-cell material such as vinyl-nitrile, which is both fire and water resistant. Further, this layer may have sound and thermo-insulating qualities and may be alternatively referred to as an acoustic layer. Finally, a helmet's comfort layer may be made of a soft material meant to fit against a rider's skin, such as cotton or other fabric blends as are known in the art. Other layers may be present as well, and some of the aforementioned layers may be deleted or combined.

Helmets usually include ear-cups, which are often molded into the rigid portions of the helmet, such as the foam layer.

The ear-cups may be static and merely provide space for a rider's ears, or they may include electronics, such as headphones, so that a rider may listen to music or communicate over an electronic communication system. In some cases, the ear-cups may be mounted to the shell of the helmet so that they can articulate and provide better comfort to riders. In other cases, the helmet may have a recess where a rider may install aftermarket ear-cups that are not a part of the helmet. Many designs are known in the art. Common to most designs is the fact that a standard ear-cup is either formed in a rigid material that is vibrationally coupled to the helmet's shell, or the ear-cup is directly connected to the helmet's shell. In both cases, vibrations from wind and other noise sources are readily transmitted from the shell of the helmet to the ear-cup and then to the motorcyclist's ear. This vibrational coupling in-turn creates irritating noise for the motorcyclist.

FIG. 1 is a perspective view of a motorcycle helmet 100. The helmet 100 comprises an outer shell 102, an acoustic layer 104, a foam layer 106, a comfort layer 108, and a passive noise reduction system 118. The passive noise reduction system 118 comprises an ear-cup 110, a coupling 116, an adjustment plate 114, and isolation mount 112. The ear-cup 110 is mounted to a coupling 116 on each side of the helmet 100. The coupling 116 is mounted to the adjustment plate 114. The coupling 116 allows the ear-cup 110 to articulate for better comfort. The adjustment plate 114 allows the position of the ear-cup 110 to be adjusted to best fit a user's ear position within the helmet 110. The adjustment plate 114 is adjustably mounted to the isolation mount 112. The isolation mount 112 may be made from a vibration dampening material so as to isolate the ear-cup 110 from the shell 102. Further, the isolation mount 112 may be molded with the interior dimension offset in relation to the exterior, and ribbed to enable multiple adjustment plate 114 mounting locations in both radial and circumferential directions relative to the motorcyclist's head. Alternatively, the adjustment plate 114 may be mounted to the isolation mount 112 by means of a press or friction fit, or other methods as are known in the art.

Note that in FIG. 1 only one ear-cup 110 is visible. However, the same assembly, shown in broken lines, is also present on the opposite side of the helmet 100. The passive noise reduction system 118 will be described in more detail below with reference to FIG. 3.

As is shown in FIG. 1, the ear-cup 110 is isolated from the shell 102 of the helmet 100 by the isolation mount 112. The isolation mount 112 is preferably made of a vibration dampening material. The vibration dampening material may prevent shell 102 vibrations from reaching a user's ear and thus may decrease the user's perception of those vibrations as noise. Thus, by mounting the ear-cup 110 to something other than the shell 102 of the helmet, and decoupling it from rigid materials that easily transmit vibrations, noise transmitted to the ear-cup 110 may be reduced. Notably, this noise reduction is accomplished without significantly reducing a motorcyclist's hearing ability through, for example, excess padding placed against the ear.

Figure 2:
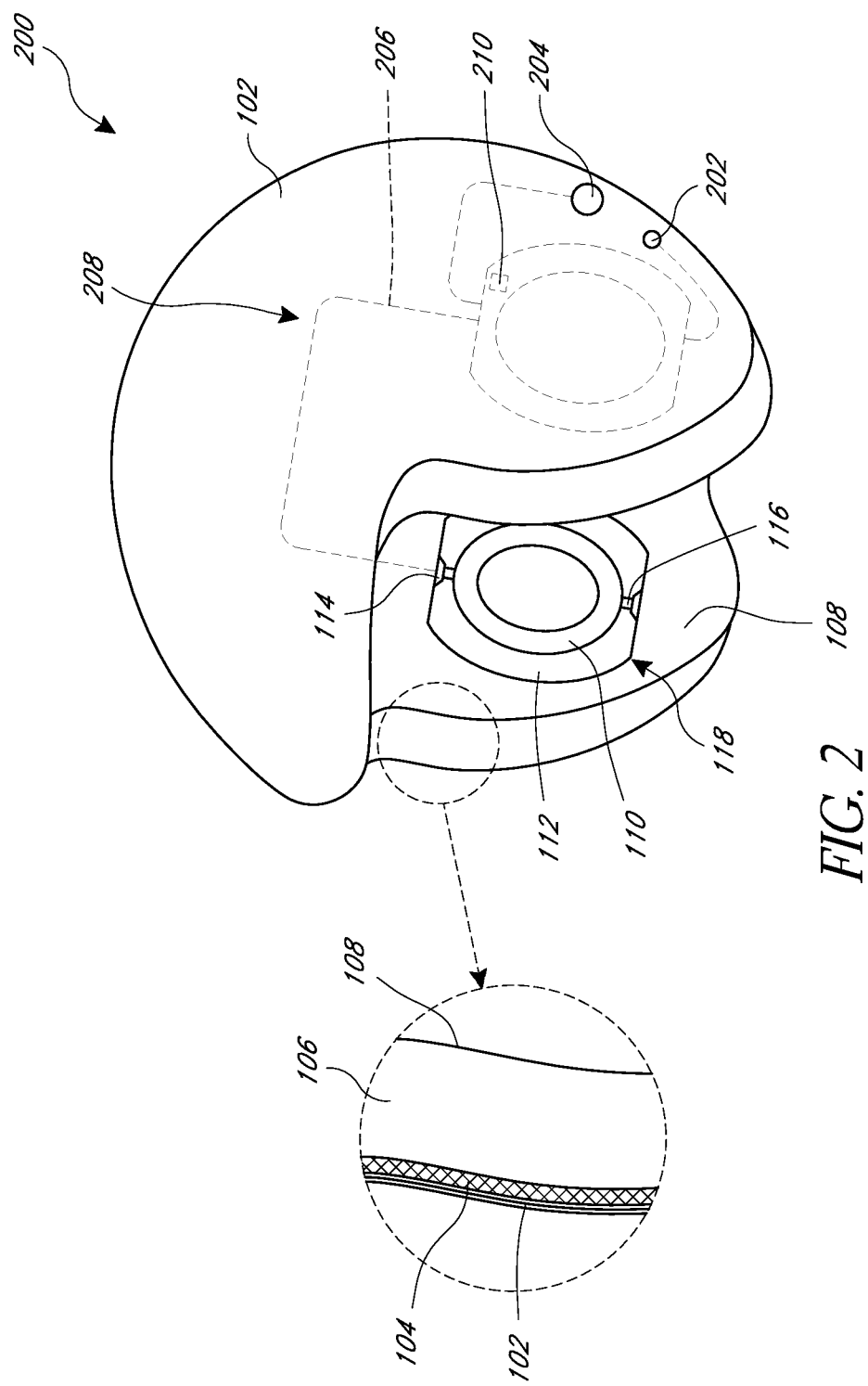
FIG. 2 is a perspective view of a motorcycle helmet with a passive noise reduction system and an active audio system.

FIG. 2 is a perspective view of a motorcycle helmet 200 which is the same as the helmet 100 described in connection with FIG. 1 except that the helmet 200 further includes an audio system 208. The audio system 208 comprises audio port 202, which provides a connection for an audio signal from, for example, a radio, a stereo, or a communication system. The audio port 202 may connect to electronics in each ear-cup 110 via electric connection 206. Each ear-cup 110 may render the audio using, for example, a speaker or other type of sound driver, built into the ear-cup 110.

Additionally, the audio system 208 may include electronics 210 that sense noise frequencies and actively cancel them in conjunction with speakers in each ear-cup 110. In this way, the benefits of the passive noise reduction system 118 may be combined with an active noise reduction system. In some embodiments, the electronics 210 components are mounted within the shell 102 of helmet 200 and may be isolated from the shell 102 by vibration dampening material. Activation switch 204 may activate or deactivate the electronics 210 of the active noise reduction system.

Figure 3A:
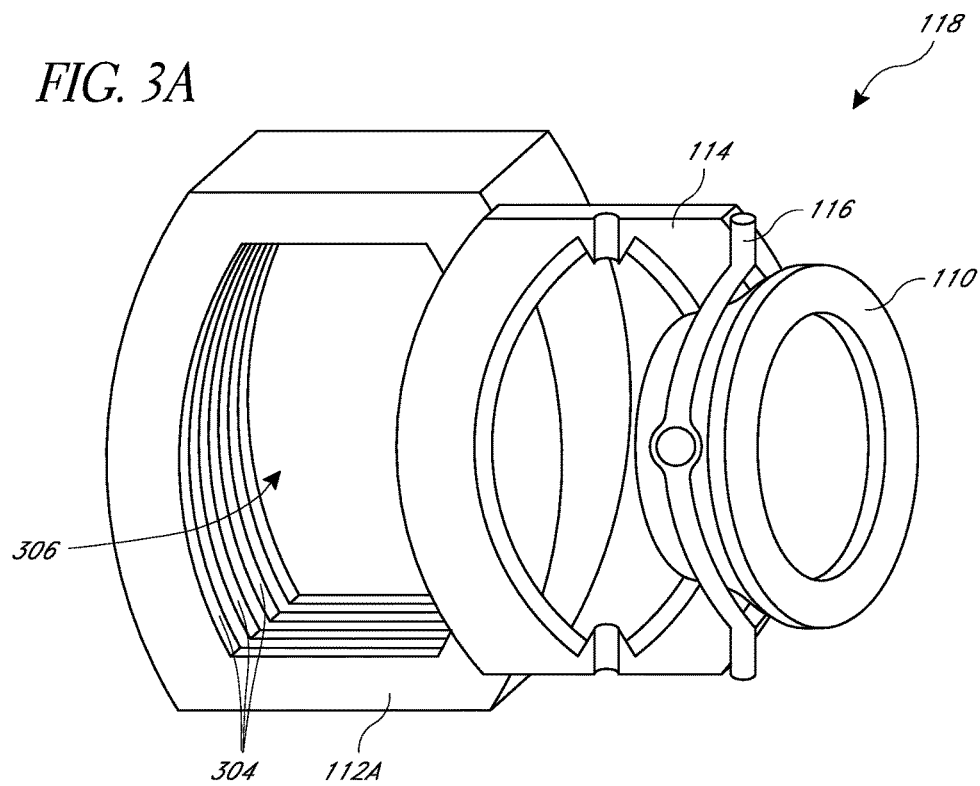
FIG. 3A is a perspective view of a passive noise reduction system for a helmet.

FIG. 3A is an exploded perspective view of the passive noise reduction system 118 from FIG. 1. As described above, the passive noise reduction system 118 includes ear-cup 110, coupling 116, adjustment plate 114 and isolation mount 112A. The ear-cup 110, which interfaces with the motorcyclist's ear, is mounted to coupling 116, which allows the ear-cup 110 to rotate up or down, i.e. about a horizontal axis. The coupling 116 mounts to the adjustment plate 114, which allow the ear-cup 110 to rotate side-to-side, i.e. about a vertical axis. Accordingly, this arrangement allows two degrees of freedom of the ear-cup 110, which increases comfort for the user.

The isolation mount 112A includes a receptacle 306 sized to receive the adjustment plate 114. The inner surface of the receptacle 306 and/or the outer surface of the adjustment plate 114 may include one or more engagement structures 304. In the illustrated embodiment, the engagement structures 304 are disposed on the isolation mount 112A. The engagement structures 304 circumscribe the inner walls of the receptacle 306 to form a plurality of ribs. Of course the engagement structures 304 need not circumscribe the entire receptacle 306. For example, the engagement structures 304 may be in the form of protrusions intermittently disposed across one or more inner walls of the receptacle 304 or other structures which are disposed so as to engage the outer perimeter of the adjustment plate 114. In some embodiments, the engagement structure 304 is an interference fit between complementary surfaces on the isolation mount 112A and the adjustment plate 114 which at least inhibits movement of the adjustment plate 114 through the receptacle 306. In this way, the engagement structure 304 allows the user to selectively locate the adjustment plate 114 within the receptacle 306.

The engagement structure 304 allows the user to adjust the mounting depth of the adjustment plate 114 within the receptacle 306 in the isolation mount 112A. In other words, the distance between the ear-cup 110 and the user's ear is adjustable to better fit the user's ears. As discussed above, the isolation mount 112A is made of a vibration dampening material so that the ear-cup 110 is better isolated from vibrations traversing the shell or other rigid parts of the helmet 100. The exterior shape of the isolation mount 112A may be dimensioned to fit within a complementary space within the helmet 100, such as shown in FIG. 1. The exterior shape of the isolation mount 112A of FIG. 3A is just one example, and those skilled in the art will appreciate that it can take many shapes. For example, another embodiment of the isolation mount 112A may have a rounded exterior shape.

Figure 3B:
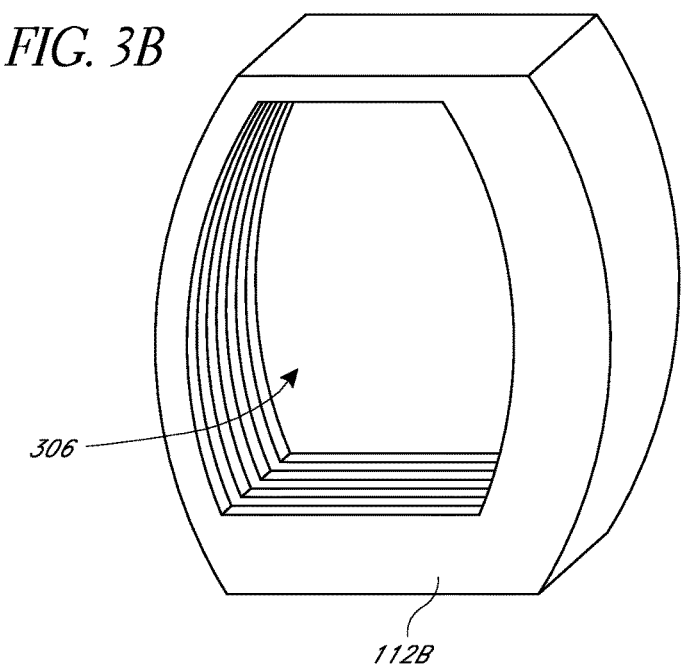
FIG. 3B is a perspective view of an alternate embodiment of an eccentric isolation mount for use with the passive noise reduction system of FIG. 3A.

FIG. 3B is a perspective view of an isolation mount 112B which is similar to the isolation mount 112A except that the receptacle 306 is offset from the center of the isolation mount 112B. For example, in the embodiment illustrated in FIG. 3B, the receptacle 306 is offset in a direction towards the upper left corner of the isolation mount 112B. In so doing, the adjustment plate 114 would fit within the isolation mount 112B at a position relatively higher and farther to the left. An advantage of this embodiment is that the isolation mount 112B may be mounted within the same helmet 100 in four different orientations. The different orientations of the isolation mount 112B results in the receptacle 306 being located at locations slightly offset from one another. For example, the isolation mount 112B may be located in the helmet 100 with the receptacle 306 offset in a direction towards the upper left corner of the isolation mount 112B. Alternatively, the isolation mount 112B may be removed from the helmet 100, rotated 180 degrees, and replaced in the helmet 100. When replaced within the helmet 100, the receptacle 306 will be slightly offset from its prior position within the helmet 100 in a direction towards the lower right corner of the isolation mount 112B. Additionally, the isolation mount 112B may be flipped over and installed into the helmet, which provides two more possible orientations.

By offsetting the receptacle 306 in the isolation mount 112B, the user can adjust the position of the ear-cup 110 within the helmet 100 to better fit a user's ear position. This adjustment can be in addition to the multi-axis swivel (up or down and side-to-side) of the ear-cup 110. The illustrated shape of the receptacle 306 in the isolation mount 112B is exemplary, and those skilled in the art will appreciate that it can take many shapes. For example, another embodiment of an isolation mount may have a rounded interior shape.

Figure 4:
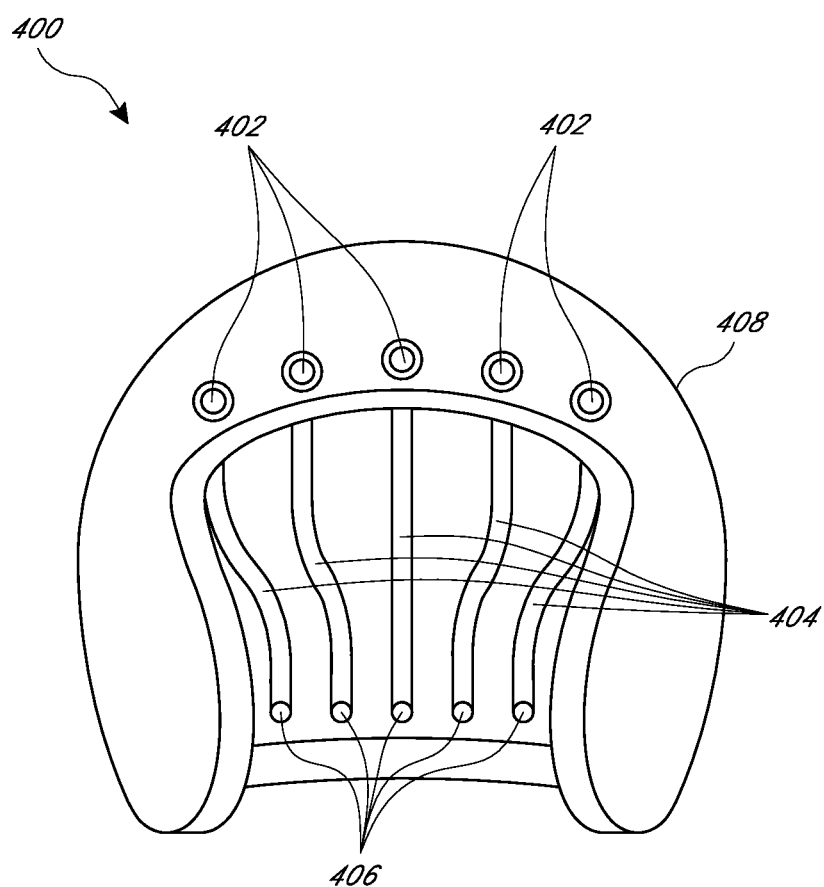
FIG. 4 is a perspective view of a noise reducing ventilation system in a helmet.

FIG. 4 is a perspective view of a helmet 400 comprising a ventilation system 408. The ventilation system 408 may be employed in a helmet that includes the passive noise reduction system 118 and/or the active noise reduction system described above.

The ventilation system 408 includes high-pressure venturi intake vents 402. The vents 402 are disposed on the front or wind-facing side of the helmet 400. Once air enters vents 402, it travels through laminar flow ducts 404 around the periphery of the helmet 400. In some embodiments, the ducts 404 are separated from the interior of the helmet 400 by a porous material, such as a cotton fabric, so that the airflow may enter the helmet all along the ducts 404. In other embodiments, the ducts 404 are completely closed off from the interior of the helmet 400. Air flowing through the ducts 404 exits at low pressure exhaust nozzles 406 and ventilates the motorcyclist's head and neck area. By reducing the pressure of the air by way of the vents 402, as it enters the helmet 400, and routing it through ducts 404 and out nozzles 406, the amount of turbulence-induced vibration (i.e. noise) is minimized while still providing adequate ventilation to the motorcyclist.

Embodiments of the helmets described in FIGS. 1-4 may include additional accessories such as visors, chin straps, buttons, eye screens, and others without departing from the scope of the invention.

The various embodiments of the helmets with noise reduction elements and techniques described above thus provide a number of ways to provide a helmet with reduced noise while in use. Of course, it is to be understood that not necessarily all such objectives or advantages may be achieved in accordance with any particular embodiment using the helmet system described herein. Thus, for example, those skilled in the art will recognize that the systems may be developed in a manner that achieves or optimizes one advantage or group of advantages as taught herein without necessarily achieving other objectives or advantages as may be taught or suggested herein. In addition, the techniques described may be broadly applied for use with a variety of helmet types.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Thus, it is intended that the scope of the systems disclosed herein disclosed should not be limited by the particular disclosed embodiments described above.

What is claimed is:

1. A passive noise cancellation system comprising:
   an isolation mount having a receptacle;
   an adjustment plate at least partially disposed in the receptacle and configured to selectively engage with the receptacle to adjust a mounting depth of the adjustment plate within the receptacle; and
   an engagement structure disposed so as to inhibit movement of the adjustment plate through the receptacle.

2. The passive noise cancellation system of claim 1 further comprising an ear-cup secured relative to the adjustment plate, the ear-cup having at least two degrees of freedom of movement.

3. The passive noise cancellation system of claim 1, wherein the engagement structure is disposed on the adjustment plate.

4. The passive noise cancellation system of claim 1, wherein the engagement structure is disposed in the receptacle.

5. The passive noise cancellation system of claim 1, wherein the engagement structure is a plurality of ribs.

6. The passive noise cancellation system of claim 1, wherein the receptacle is offset from a center of the isolation mount.

7. A passive noise cancellation system comprising:
   an isolation mount having a receptacle;
   an adjustment plate disposed within the receptacle and configured to selectively engage with the receptacle to adjust a mounting depth of the adjustment plate within the receptacle;
   a coupling secured to the adjustment plate; and
   an ear-cup secured to the coupling so as to allow the ear-cup to articulate relative to the coupling.

8. The passive noise cancellation system of claim 7, wherein the adjustment plate is adjustably mounted to the isolation mount.

9. The passive noise cancellation system of claim 7, wherein the isolation mount is made from a vibration dampening material.

10. The passive noise cancellation system of claim 7, wherein an interior dimension of the isolation mount is offset from an exterior dimension of the isolation mount.

11. The passive noise cancellation system of claim 7, wherein the adjustment plate is mounted to the isolation mount by a friction fit.

12. The passive noise cancellation system of claim 7 further comprising an engagement structure, the engagement structure configured to inhibit movement of the adjustment plate through the receptacle.

13. The passive noise cancellation system of claim 12, wherein the engagement structure is a plurality of protrusions.

14. The passive noise cancellation system of claim 12, wherein the engagement structure is disposed on the adjustment plate.

15. The passive noise cancellation system of claim 12, wherein the engagement structure is disposed in the receptacle.

16. The passive noise cancellation system of claim 12, wherein the engagement structure is a plurality of ribs.

17. The passive noise cancellation system of claim 16, wherein the plurality of ribs is configured to secure the adjustment plate at multiple locations.

18. A passive noise cancellation system comprising:
   an isolation mount having a receptacle, the receptacle being offset from a center of the isolation mount;
   an adjustment plate disposed within the receptacle and configured to selectively engage with the receptacle to adjust a mounting depth of the adjustment plate within the receptacle;
   an engagement structure disposed so as to inhibit movement of the adjustment plate through the receptacle;
   a coupling secured to the adjustment plate; and
   an ear-cup secured to the coupling.

19. The passive noise cancellation system of claim 18, wherein the adjustment plate is adjustably mounted to the isolation mount.

20. The passive noise cancellation system of claim 18, wherein the isolation mount is made from a vibration dampening material.

\* \* \* \* \*